(12) United States Patent
Renesto et al.

(10) Patent No.: US 9,272,149 B2
(45) Date of Patent: Mar. 1, 2016

(54) DEVICE FOR ASSESSMENT AND THERAPY OF TEMPORAL VENTRICULAR DESYNCHRONIZATION

(71) Applicant: SORIN CRM S.A.S., Clamart (FR)

(72) Inventors: Fabrizio Renesto, Clamart (FR); Christine Henry, Clamart (FR)

(73) Assignee: SORIN CRM S.A.S., Clamart (FR)

( * ) Notice: Subject to any disclaimer, the term of this patent is extended or adjusted under 35 U.S.C. 154(b) by 23 days.

(21) Appl. No.: 14/042,385

(22) Filed: Sep. 30, 2013

(65) Prior Publication Data

US 2014/0094870 A1 Apr. 3, 2014

(30) Foreign Application Priority Data

Oct. 1, 2012 (FR) ...................................... 12 59252

(51) Int. Cl.
| | |
|---|---|
| *A61N 1/365* | (2006.01) |
| *A61N 1/368* | (2006.01) |
| *A61N 1/362* | (2006.01) |
| *A61B 5/11* | (2006.01) |
| *A61B 5/02* | (2006.01) |
| *A61B 5/0215* | (2006.01) |
| *A61B 5/0452* | (2006.01) |
| *A61B 5/053* | (2006.01) |

(52) U.S. Cl.
CPC ........ *A61N 1/36585* (2013.01); *A61B 5/02028* (2013.01); *A61B 5/1107* (2013.01); *A61N 1/3682* (2013.01); *A61N 1/3684* (2013.01); *A61B 5/0215* (2013.01); *A61B 5/0452* (2013.01); *A61B 5/0538* (2013.01)

(58) Field of Classification Search
CPC ............ A61N 1/3627; A61N 1/36585; A61N 1/3684; A61N 1/3682; A61N 1/36571; A61N 1/36578; A61B 5/02028; A61B 5/0452; A61B 5/1107
See application file for complete search history.

(56) References Cited

U.S. PATENT DOCUMENTS

| 7,212,861 | B1 | 5/2007 | Park et al |
| 2005/0027320 | A1* | 2/2005 | Nehls et al. ...................... 607/9 |
| 2008/0183072 | A1 | 7/2008 | Robertson et al. |

FOREIGN PATENT DOCUMENTS

| EP | 0 515 319 A2 | 11/1992 |
| EP | 1 108 446 | 6/2001 |
| EP | 1 736 203 | 12/2006 |

(Continued)

OTHER PUBLICATIONS

Preliminary Search Report for French Patent Application No. 1259252, dated Jul. 25, 2013, 3 pages.

*Primary Examiner* — William Levicky
(74) *Attorney, Agent, or Firm* — Foley & Lardner LLP (57) ABSTRACT

A device includes a hemodynamic sensor measuring blood flow in the left chambers of a myocardium, at least one motion sensor measuring a displacement of the walls of the left ventricle of the myocardium, a first analysis module determining a time of closure of the aortic valve based on a signal of the hemodynamic sensor, a second analysis module determining a time of peak contraction of the left ventricle based on a signal from the motion sensors, and a third analysis module determining a time between the moment of peak contraction of the left ventricle and the moment of closure of the aortic valve. If the peak of contraction of the left ventricle is after the instant of closure of the aortic valve, the device adjusts the inter-ventricular delay and/or the atrioventricular delay to minimize or cancel the time disparity.

12 Claims, 4 Drawing Sheets

(56) References Cited

FOREIGN PATENT DOCUMENTS

| EP | 2 092 885 A1 | 8/2009 |
| EP | 2 357 020 | 8/2011 |
| EP | 2 495 013 | 9/2012 |
| WO | WO-95/27531 | 10/1995 |

* cited by examiner

DEVICE FOR ASSESSMENT AND THERAPY OF TEMPORAL VENTRICULAR DESYNCHRONIZATION

CROSS-REFERENCE TO RELATED PATENT APPLICATIONS

This application claims the benefit of and priority to French Patent Application No. 1259252 filed Oct. 1, 2012, the entirety of which is incorporated by reference herein.

BACKGROUND

The present disclosure relates generally to medical devices for use in patient care. The present disclosure relates more particularly to a medical device for the diagnosis and treatment of ventricular desynchronization in a patient.

Ventricular desynchronization is a heart condition that typically occurs in two forms: (1) spatial desynchronization and (2) temporal desynchronization. Spatial desynchronization and temporal desynchronization may occur independently or in combination with each other.

In spatial desynchronization, a cardiac conduction disorder causes a delay in the contraction of one of the heart ventricles (i.e., the left ventricle or the right ventricle) relative to the contraction of the other ventricle, leading to deterioration in the hemodynamic status of the patient. U.S. Patent Application Publication No. 2005/0027320 A1 (granted as U.S. Pat. No. 7,092,759) discloses a device for the detection of the desynchronization between the two ventricles (i.e., spatial desynchronization). The disclosed device allows for the assessment and application of an appropriate stimulation therapy, including the optimization of the interventricular delay (VVD).

Temporal desynchronization is characterized by a late contraction of all or part of the left ventricle in relation to the closure of the aortic valve. In temporal desynchronization, some segments of the ventricular wall are still in a contracted state during the diastolic phase (i.e., after the ejection of blood into the aorta, during the closing of the aortic valve) and, in extreme cases, after the opening of the mitral valve, (i.e., at the beginning of the phase of passive filling of the left ventricle with blood from the left atrium). Temporal ventricular synchronization may be characterized by the presence of diastolic contraction (i.e., with setback) of some segments of the left ventricle with an antagonistic effect on the hemodynamic activity and a decrease in ejection fraction, considered the reference hemodynamic parameter.

These ventricular desynchronizations can be treated by a Cardiac Resynchronization Therapy (CRT) or Bi-Ventricular Pacing (BVP) technique consisting of implanting a device with electric leads (i.e., electrodes) in the patient to stimulate one or both ventricles at various ventricular locations. The device applies an appropriate interventricular delay (VVD) between the respective moments of stimulation of the right and left ventricles. The VVD may be adjusted to resynchronize the contraction of the ventricles with fine tuning of the patient's hemodynamic status. The VVD can be zero, positive (i.e., the left ventricle being stimulated after the right ventricle) or negative (i.e., the right ventricle being stimulated after the left ventricle).

Various global assessment techniques of hemodynamic function in a patient are known. For example, European Patent Application Publication No. 1108446 A1 (ELA Medical S.A.) evaluates hemodynamic function using an intracardiac bio-impedance measurement. The intracardiac bio-impedance measurement is a parameter indicative of the cardiac output and thus of the ejection fraction. Another example is provided in European Patent Application Publication No. 2092885 A1 (Sorin CRM S.A.S), which extracts information from an endocardial acceleration signal and combines various indicators representative of the patient's hemodynamic status. However, these devices operate a non-specific diagnosis of ventricular desynchronization, without distinction between temporal and spatial desynchronization.

International Publication No. WO 95/27531 A1 discloses a device, provided in particular with one or more velocity or acceleration sensors measuring the displacement of the heart wall in order to determine whether myocardial contractions are occurring. The sensor can be an endocardial acceleration (EA) sensor which produces a signal reflecting, in the form of two peaks, the two heart sounds produced by the closing of the mitral valve and at the opening of the aortic valve. Measuring the height of one or the other peak of the EA signal provides an indication of whether any mechanical activity of the heart is occurring. In the absence of mechanical activity of the heart, the device issues an appropriate bradycardia therapy (e.g., conventional stimulation of the DDD or DDI type). However, in the presence of a mechanical activity, therapy is inhibited so as not to interfere with the spontaneous contractions of the myocardium.

U.S. Pat. No. 7,212,861 and European Patent Application Publication No. 2495013 describe various techniques for search of an optimal stimulation configuration based on the detection of the mechanical activity of the ventricle. However, like the documents, they do not consider the specific diagnosis or treatment of any possible ventricular desynchronization.

Current treatments and devices do not provide a specific method to diagnose the temporal desynchronization of the ventricle, regardless of any consideration relating to possible spatial desynchronization. In particular, current treatments and devices do not distinguish between temporal and spatial desynchronization or apply differentiated therapies according to the type of disorder. While it is generally sufficient to apply biventricular pacing with VVD (e.g., as described in U.S. Patent Application Publication No. 2005/0027320 A1) to address spatial desynchronization, the treatment of temporal desynchronization—which involves only one ventricle—may require a much finer adjustment of various stimulation parameters. The stimulation parameters may include, for example, the atrioventricular delay (AVD) and/or a combination of AVD and VVD. The specific detection of a temporal desynchronization may help to treat, or possibly even cure, a disorder which is untreated or inadequately treated by conventional CRT therapy.

OBJECT AND SUMMARY

The present invention relates to a device for evaluating and treating ventricular desynchronization in a patient. The device includes a hemodynamic sensor for delivering a signal representative of blood flow in the left cavities of the myocardium, at least one motion sensor for delivering a signal representative of a displacement of the walls of the left ventricle of the myocardium, a first analysis means for determining a closing moment of the aortic valve based on the signal of the hemodynamic sensor, a second analysis means for determining a contraction peak moment of the left ventricle based on the signal(s) of the motion sensor(s), and a third analysis means for determining the relative temporal position of the moment of the contraction peak of the left ventricle relative to the aortic valve closing moment.

The hemodynamic sensor may be at least one of an implantable or external endocardial acceleration sensor, an implantable bioimpedance sensor, an implantable or external T wave detection sensor, and an implantable ventricular pressure sensor.

The motion sensor may be at least one of a motion sensor implantable in an endocardial, epicardial or endocoronary site, an external motion sensor, and a field tomography signal collection sensor.

In some embodiments, the implantable hemodynamic sensor is a sensor for delivering an endocardial acceleration (EA) signal. The first analysis means may be means for isolating a component (EA2) of the EA signal. The isolated signal component EA2 may correspond to the second peak of endocardial acceleration associated with the ventricular isovolumetric relaxation over a cardiac cycle between two successive ventricular events. In some embodiments, the beginning of the EA2 signal component may be used as the moment of closure of the aortic valve. In some embodiments, the moment of closure of the aortic valve may be determined by identifying a moment at which an energy envelop based on the EA2 signal component crosses an energy threshold.

In some embodiments, the device of the invention can also be used for therapy of temporal ventricular desynchronization. To treat temporal ventricular desynchronization, the device may include a bi-, tri- or multiventricular stimulation means for delivering stimulation pulses to electrodes respectively located in at least one right ventricular pacing site and in at least one left ventricular pacing site. The stimulation pulses may be delivered according to a current stimulation configuration with application of a modifiable interventricular delay VVD and/or a modifiable atrioventricular delay AVD. If the third means of analysis determines that the moment of the peak contraction of the left ventricle is posterior to the moment of closure of the aortic valve, then the VVD and/or the AVD of the current stimulation configuration can be adjusted to reduce or cancel the delay of the peak of contraction of the left ventricle after the closure of the aortic valve.

In some embodiments, the device can be used to diagnose and treat both temporal ventricular desynchronization and spatial ventricular desynchronization. For example, the device may include at least two motion sensors for delivery of signals representative of the respective displacements of the walls of the right and left ventricles of the myocardium. The second analysis means may determine the moments of the respective contraction peaks of the left and right ventricles. The device may include a means for assessing the spatial ventricular desynchronization means in the patient by determining a concomitance defect in the respective contraction peaks of the left and right ventricles.

For treating the spatial desynchronization thus diagnosed, the device may include a bi-, tri- or multiventricular pacing means for delivering stimulation pulses to be respectively applied to electrodes implanted in at least one right ventricular stimulation site and in at least one left ventricular stimulation site. The stimulation pulses may be delivered according to a current stimulation configuration with application of a modifiable interventricular delay VVD and/or a modifiable atrioventricular delay AVD. If the means for assessing the temporal desynchronization determine that the moments of the contraction peaks of the left and right ventricles are both posterior to the moment of closure of the aortic valve, the VVD and/or the AVD of the current stimulation configuration can be changed and in a direction that reduces and cancels the delay of these two contraction peaks after closure of the aortic valve and/or reduces the temporal gap between these two contraction peaks.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

The present invention relates to systems and methods for evaluating and treating temporal ventricular desynchronization. The systems and methods described herein may be used to control an implantable device (e.g., a cardiac pacemaker or a defibrillator/cardioverter, etc.) based on signals collected by the device (e.g., via endocardial leads and/or one or more implanted sensors) for the evaluation and therapy of temporal ventricular desynchronization.

The present invention may particularly be applied to implantable devices such as those of the Reply and Paradym device families produced and marketed by Sorin CRM, Clamart France, formerly known as ELA Medical, Montrouge, France. These devices generally include programmable microprocessor circuitry configured to receive, format, and process electrical signals. The electrical signals may be collected (e.g., detected) by implanted electrodes in communication with the devices. The devices are configured to deliver stimulation pulses to the electrodes. It is possible to transmit (e.g., by telemetry) software that will be stored in a memory of the implantable devices and executed to implement the functions of the invention that will be described herein. The adaptation of these devices to implement the functions and features of the present invention is believed to be within the abilities of a person of ordinary skill in the art, and therefore will not be described in detail.

The systems and methods described herein may use a device that is the same or similar to the device described in International Publication No. WO 95/27531 A1, incorporated by reference herein in its entirety. For example, the device may include an hemodynamic sensor delivering a signal representative of a blood flow in the left chambers of the myocardium; at least one motion sensor delivering a signal representative of a displacement of the walls of the left ventricle of the myocardium; first analysis means for determining a moment of closure of the aortic valve from the signal of the hemodynamic sensor; second analysis means for detecting and evaluating a contraction peak of the left ventricle from signal(s) of the motion sensor(s); and bi-, tri- or multiventricular stimulation means for delivering stimulation pulses to be applied to electrodes located respectively in at least one right ventricular pacing site and in at least one left ventricular pacing site. The stimulation pulses may be applied according to a current stimulation configuration with application of at least one modifiable inter-ventricular delay VDD and/or one modifiable atrioventricular delay AVD.

In some embodiments, the second analysis means determines a timing of said peak of contraction of the left ventricle. In some embodiments, the device further includes a third analysis means for the measure of a temporal shift between the instant of the peak of contraction of the left ventricle and the instant of closure of the aortic valve. The device may further include means to change the VVD and/or AVD or the current stimulation configuration in a direction reducing and canceling the delay of the peak of contraction of the left ventricle after closure of the aortic valve. The stimulation configuration may be changed if the third analysis means determines that the instant of the peak of the left ventricular contraction is later than the instant of closure of the aortic valve.

The method of the invention is primarily implemented by software means, using appropriate control methods (e.g., processes, algorithms, techniques, etc.) executed by a microcontroller or a digital signal processor. For the sake of clarity, the various processing steps will be decomposed and schematized by a number of distinct functional blocks. However, this representation is merely illustrative. In some embodiments, the various functions (e.g., data collection, signal processing, output generation, etc.) may be implemented by one or more software modules within the implant and/or the external device.

Figure 1:
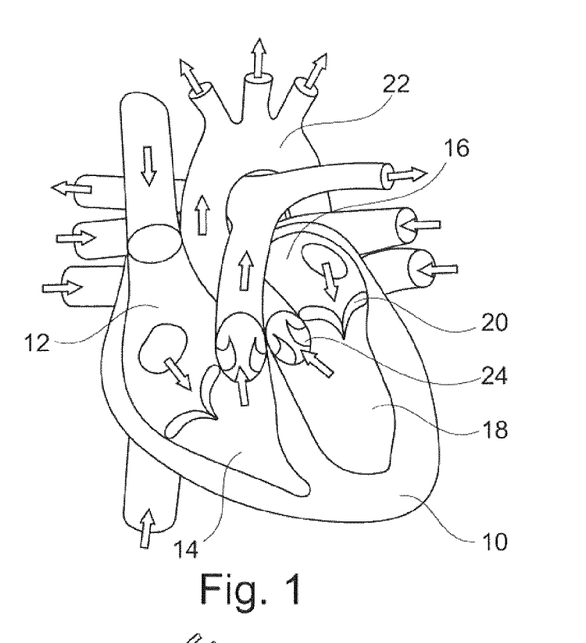
FIG. 1 is a drawing of a heart showing heart chambers and the associated valves, according to an exemplary embodiment.

Referring now to FIG. 1, an illustration of the cavities and valves of the heart 10 are shown, according to an exemplary embodiment. Heart 10 is shown to include a right atrium 12, a right ventricle 14, a left atrium 16, and a left ventricle 18. Mitral valve 20 (i.e., an atrioventricular valve) is located between the left atrium 16 and the left ventricle 18. Aortic valve 24 (i.e., a semilunar valve) is located between the left ventricle 18 and the aorta 22.

In some embodiments, the systems and methods of the present invention are capable of monitoring changes in blood flow in the left cavities (i.e., left atrium 16 and left ventricle 18), the wall motions of the left ventricle 18, and/or the movements of the wall of the right ventricle 14.

Figure 2:
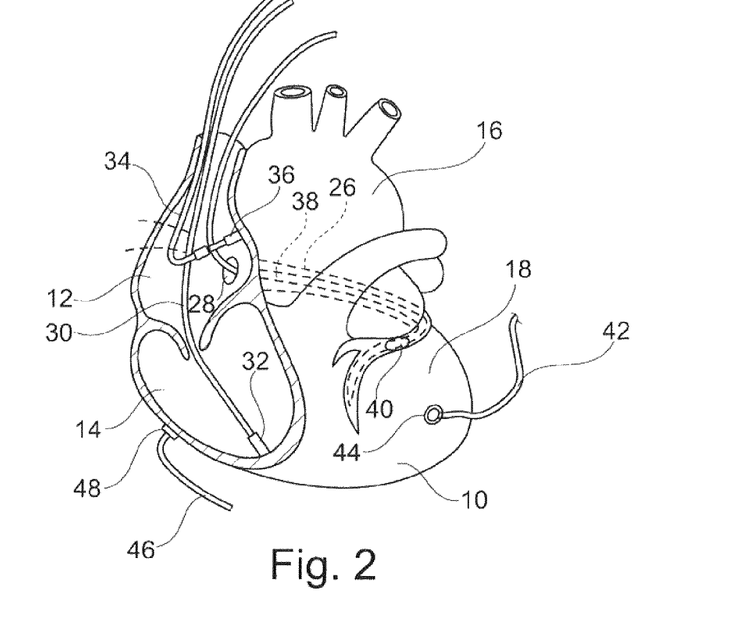
FIG. 2 illustrates a heart paired with various leads equipped with hemodynamic and motion sensors, according to an exemplary embodiment.

Referring now to FIG. 2, heart 10 can be monitored by various sensors connected to heart 10 by leads. These leads may be endocardial leads introduced into the right atrium 12 and/or the right ventricle 14, epicardial leads attached to the outer wall of the myocardium, or endocoronary leads arranged vis-à-vis the left cavities. The leads may be introduced into a vein 26 of the coronary venous system via the coronary sinus 28 opening into the right atrium 12.

In some embodiments, one or more of the leads connect to a hemodynamic sensor. The hemodynamic sensor may provide a signal representative of changes in blood flow at the time of closure of the aortic valve 24. In some embodiments, the sensor may be arranged, for example, on an endocardial lead 30 terminating at the apex of the ventricle 14 (i.e., sensor 32) and configured to sense an endocardial acceleration (EA).

The one or more leads may include an atrial lead 34. Atrial lead 34 may be connected to an endocardial acceleration sensor 36 placed against the wall of the right atrium 12. An EA sensor may include, for example, an accelerometer integrated into the head of an endocardial lead, as described in European Patent Application Publication No. 0515319 A1 (Sorin Biomedica Cardio SpA).

In some embodiments, the hemodynamic sensor includes an external EA sensor placed on the patient's thorax, an intracardiac bioimpedance implantable sensor, an implantable or external sensor for detection of the T-wave of the electrocardiographic signal, and/or a ventricular pressure implantable sensor. These additional sensors may be included in addition to or in place an EA sensor integrated into an endocardial lead.

In some embodiments, the device includes a motion sensor configured to deliver a signal representative of a displacement of the walls of the left ventricle 18. The motion sensor may be placed, for example, on an endocoronary lead 38 at one or more locations 40 disposed against the wall of the left ventricle 18. Alternatively or in addition, it is possible to use an epicardial lead 42 equipped with an end sensor 44 placed against the wall of the left ventricle 18.

In some embodiments, the device includes an epicardial lead 46 equipped with an end sensor 48 attached to an outer wall of the right ventricle 14. Sensor 48 may be used to measure the motion of the right ventricle.

In some embodiments, the device uses multiple motion sensors placed in different parts of the wall of the left ventricle 18 in order to more precisely analyze the movements of the different segments of the left ventricular wall. These various sensors can be placed on the same lead (e.g., endocoronary lead 38) or on different leads (e.g., endocoronary lead 38 and epicardial lead 42, etc.).

In some embodiments, various alternative techniques can be used to obtain a representation of the motion of the walls of the left ventricle 18. For example, the device may use electrotomographic analysis as described in U.S. Patent Application Publication No. 2008/0183072 A1, incorporated by reference herein for its description thereof.

The basic idea of the invention is to obtain an indication of the time of closure of the aortic valve. As described in greater detail below, the time of closure of the aortic valve may be obtained from the signal representative of the flow of blood in the left cavities delivered by the hemodynamic sensor. The time of closure of the aortic valve may be used as a reference marker for the diagnosis of temporal synchronization. For example, the reference marker (i.e., defined by the time of closure of the aortic valve) may be compared with the signal delivered by the motion sensor of the left ventricle to determine whether or not there is a state of contraction of the left ventricle posterior to this temporal marker. If so, temporal ventricular desynchronization may be diagnosed and appropriate measures can be taken after the diagnosis in an attempt to reduce or eliminate this pathological phenomenon.

Figure 3:
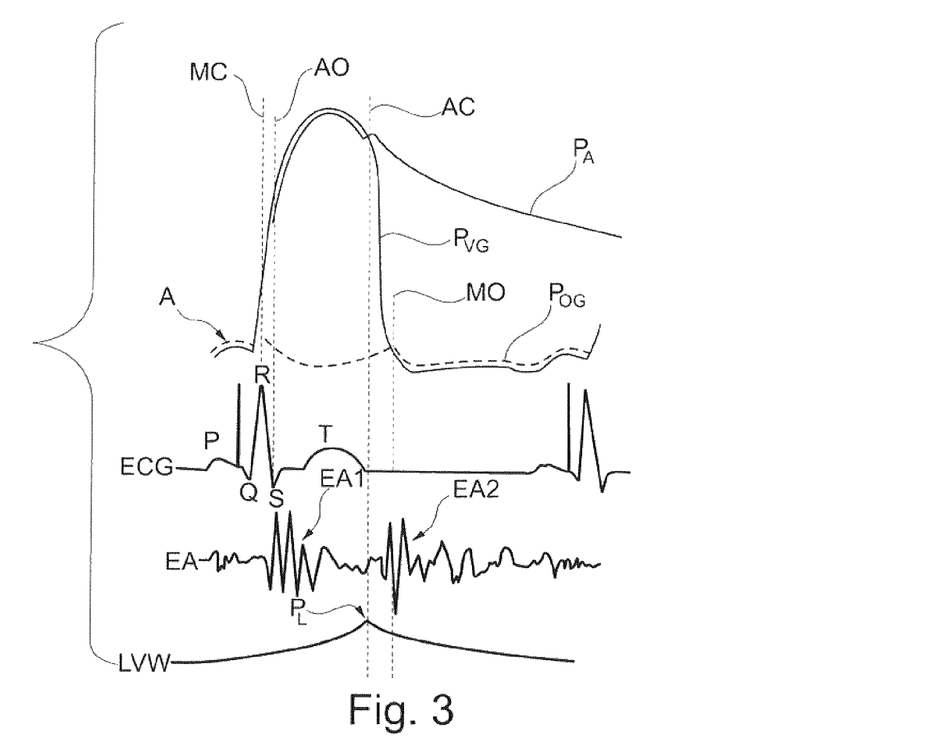
FIG. 3 is a series of graphs illustrating four different characteristic signals that can be collected during a cardiac cycle, according to an exemplary embodiment.
Figure 4:
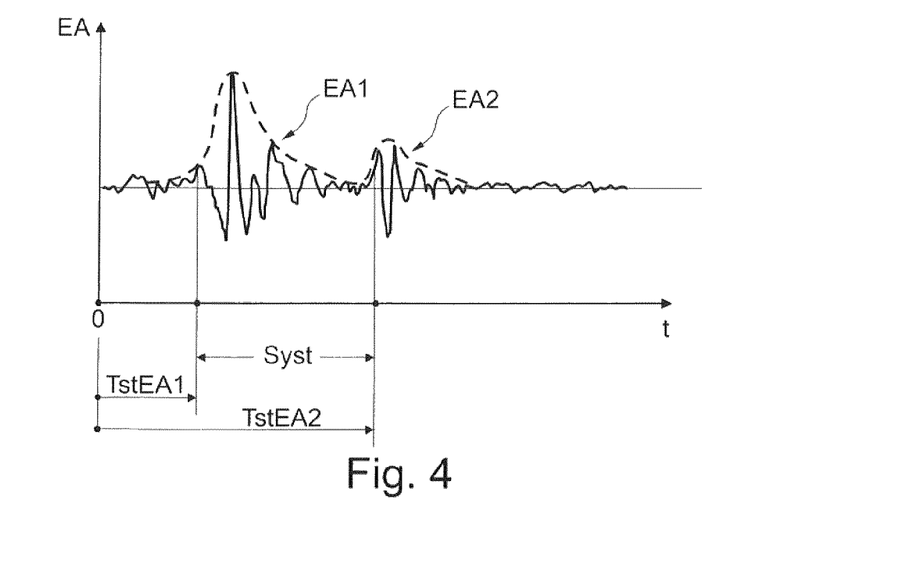
FIG. 4 shows in more detail the shape of the endocardial acceleration signal over a given cycle, with the various temporal markers used by the invention, according to an exemplary embodiment.

Referring now to FIGS. 3 and 4, a method to determine the time of closure of the aortic valve will now be explained. Referring specifically to FIG. 3, several different signals characterizing the activity of the heart during a cardiac cycle are shown, according to an exemplary embodiment. FIG. 3 is shown to include a profile of intracardiac pressures $P_A$, $P_{VG}$ $P_{OG}$. The characteristic $P_A$ corresponds to the aortic pressure, $P_{VG}$ corresponds to left ventricular pressure, and $P_{OG}$ corresponds to left atrium pressure. Pressures $P_A$, $P_{VG}$ $P_{OG}$ vary as heart 10 goes through the following phases: A (contraction of the left atrium), MC (closure of the mitral valve), AO (opening of the aortic valve), AC (closure of the aortic valve), and MO (opening of the mitral valve).

FIG. 3 is shown to further include a graph of surface electrocardiogram (ECG) with the P wave corresponding to the depolarization of the atria, the QRS complex corresponding to the depolarization of the ventricles, and the T wave corresponding to the ventricular repolarization.

FIG. 3 is shown to further include a collected endocardial acceleration (EA) signal and a signal LVW from a motion sensor. The endocardial acceleration signal EA forms two main components in a given cardiac cycle, corresponding to the two major heart sounds (e.g., S1 and S2 sounds of the phonocardiogram). It is possible to recognize each component in the cardiac cycle. The signal LVW of the motion sensor represents the displacements of the left ventricular wall. Signal LVW has a peak ($P_L$) marking the end of the contraction of all segments of the left ventricle.

Referring specifically to FIG. 4, the variations of the EA signal during a cardiac cycle are more precisely illustrated, according to an exemplary embodiment. The EA signal is shown to include an EA1 component and an EA2 component. The EA1 component begins after the QRS complex and is caused by a combination of the closing of the atrioventricular valves (i.e., the mitral and tricuspid valves), the opening of the semilunar valves (i.e., aortic and pulmonary valves) and the contraction of the left ventricle. The EA2 component occurs during the phase of isovolumetric ventricular relaxation. The EA2 component accompanies the end of ventricular systole and is mainly produced by the closing of the aortic and pulmonary valves.

A characteristic temporal marker correlated with the closure of the aortic valve can be extracted from the EA signal shown in FIGS. 3 and 4. Specifically, the temporal marker can be extracted from the EA2 component shown in FIG. 4. The characteristic temporal marker may correspond to a time indicated by the dotted line labeled AC in FIG. 3.

Analysis of the EA signal is preferably determined by averaging the EA signal over several cycles (e.g., typically three to five cycles). The EA signal may be analyzed and/or averaged using the technique described in European Patent Application Publication No. 2092885 A1 (ELA Medical), incorporated by reference herein for its description thereof. Such a technique may be useful for eliminating cycle-by-cycle variations in time by readjusting the successive components before averaging.

In some embodiments, the EA signal is continuously collected. The EA signal may be processed by cutting (e.g., splitting, dividing, etc.) the EA signal into sub-signals. Each sub-signal may correspond to the duration of a cardiac cycle and may be identified by cycle start markers (e.g., marking a beginning of the cardiac cycle) for performing the cutting. The temporal markers of the start cycle can be provided by the implanted device which, according to the operating mode, stores the moments of V stimulation or the moments of detection of the R wave.

Processing the EA signal may further include segmenting each of the sub-signals to individualize the EA1 and EA2 components in a given temporal window. For each of the components EA1 and EA2, processing may include searching for a correlation peak relative to the EA1 or EA2 components of the other collected cycles, calculating a temporal offset, and applying the calculated temporal offset to the current EA1 or EA2 component. Applying the temporal offset may align the EA1 or EA2 component with respect to the other. The analysis processing of the EA signal can then be run on the successive EA1 and EA2 components, with elimination of the bias cycle to cycle variability through this preprocessing.

In some embodiments, processing the EA signal includes determining the start time $T_{stEA2}$ of the EA2 component. Start time $T_{stEA2}$ can be obtained, for example, by thresholding an energy envelope (e.g., shown as a dashed line in FIG. 4). The energy envelope may be obtained by squaring the value of the signal samples and applying a smoothing window (e.g., 100 ms) to smooth the energy envelope. The time $T_{stEA2}$ may be identified by comparing the magnitude of the energy envelope to a threshold value. The threshold value may correspond to approximately 10% of the maximum energy associated with the EA2 component.

Figure 5:
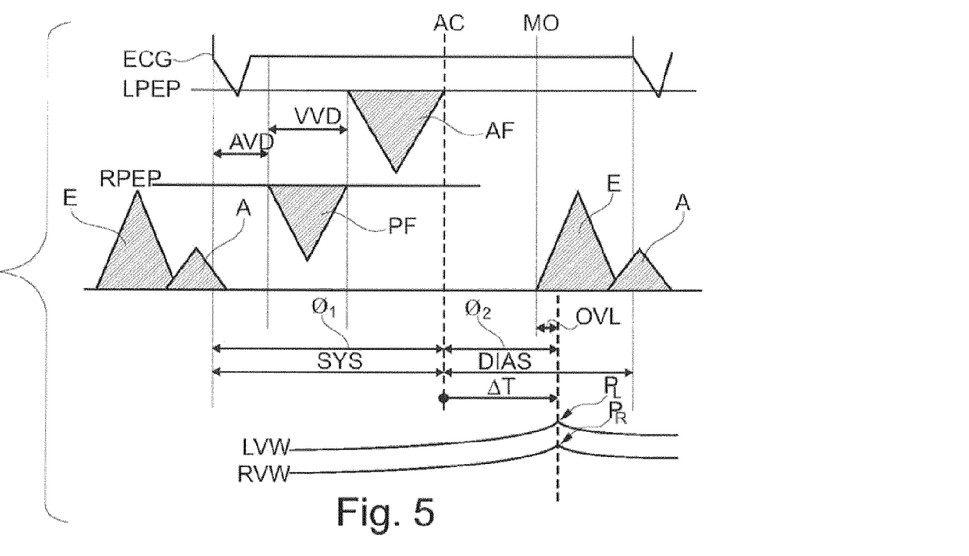
FIG. 5 is a representation in an echocardiographic diagram of a typical situation of temporal desynchronization of the left ventricle, according to an exemplary embodiment.

Referring now to FIG. 5, various parameters of a typical temporal desynchronization pathology of the left ventricle are shown, according to an exemplary embodiment. FIG. 5 shows an echocardiographic chart with several timing diagrams. The timing diagrams are shown to include an ECG signal marking the start of the atrial contraction, a left pre-ejection phase LPEP showing the aortic flow AF, a right pre-ejection phase RPEP showing the pulmonary flow PF, a phase of post-discharge with the E wave corresponding to the passive filling and the A wave corresponding to the contribution to filling of the atrial contraction, and LVW and RVW signals respectively delivered by the motion sensors of the walls of the left ventricle and the right ventricle.

The end of the flow of blood into the aorta (i.e., the end of the AF flows, marked by dashed line AC) marks the completion of the systolic phase SYS. The end of the flow of blood into the aorta also marks the beginning of the diastolic phase DIAS, after closure of the aortic valve at time AC.

The last two timing diagrams LVW and RVW have respective peaks $P_L$ and $P_R$. In FIG. 5, peaks $P_L$ and $P_R$ are concurrent, which means that the walls of the left ventricle and of the right ventricle complete their contraction at the same time. When $P_L$ and $P_R$ are concurrent, there is no spatial desynchronization. However, FIG. 5 shows a temporal desynchronization, since the peaks $P_L$ and $P_R$ (which mark the end of the contraction of the ventricles) are after the closure of the aortic valve AC. Ideally, peaks $P_L$ and $P_R$ should be concurrent with this closure, with a delay $\Delta T$.

Still referring to FIG. 5, an overlap phenomenon OVL is shown. The overlap existsto the extent that ventricular contraction peaks $P_L$ and $P_R$ are after the time of opening of the mitral valve MO. When peaks $P_L$ and $P_R$ occur after the opening of the mitral valve, the contraction of the ventricles encroaches on the passive filling of the ventricle E. In FIG. 5, peaks $P_L$ and $P_R$ occur at the wrong time (i.e., too late) compared to the normal hemodynamic behavior. In other words, the normal systolic contraction Ø1 of the left ventricle is extended by a pathologic diastolic contraction Ø2, which should be diagnosed and treated to restore proper functioning of the heart, particularly from the hemodynamic point of view.

Figure 6:
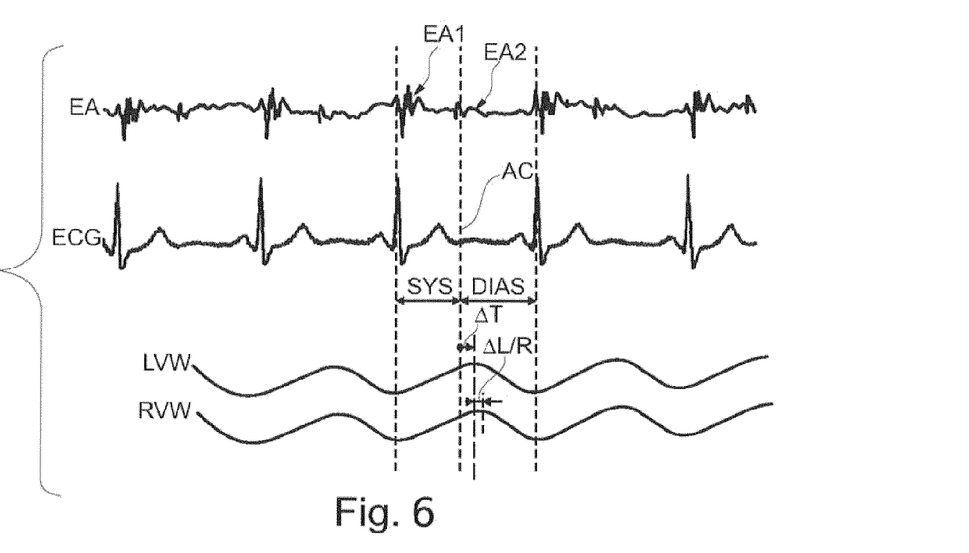
FIG. 6 is a series of four graphs illustrating a typical situation of dual, temporal and spatial, desynchronization of the ventricles, according to an exemplary embodiment.

Referring now to FIG. 6 another representation of a situation of ventricular desynchronization is shown, according to an exemplary embodiment. FIG. 6 shows the Endocardial acceleration EA, the electrocardiogram ECG, and the LVW and RVW signals representative of the movements of the walls of the respective left and right ventricles.

FIG. 6 illustrates both a temporal desynchronization and a spatial desynchronization. The temporal desynchronization is evident by the delay $\Delta T$ between the peak of the LVW signal and the second peak EA2 of the EA signal. The second peak EA2 of the EA signal corresponds to the closure of the aortic valve AC. The spatial desynchronization $\Delta L/R$ is evident by the relative shift of the peaks LVW and RVW. As shown in FIG. 6, the contraction of the right ventricle (i.e., the peak of RVW) is later than that of the left ventricle (i.e., the peak of LVW).

Figure 7:
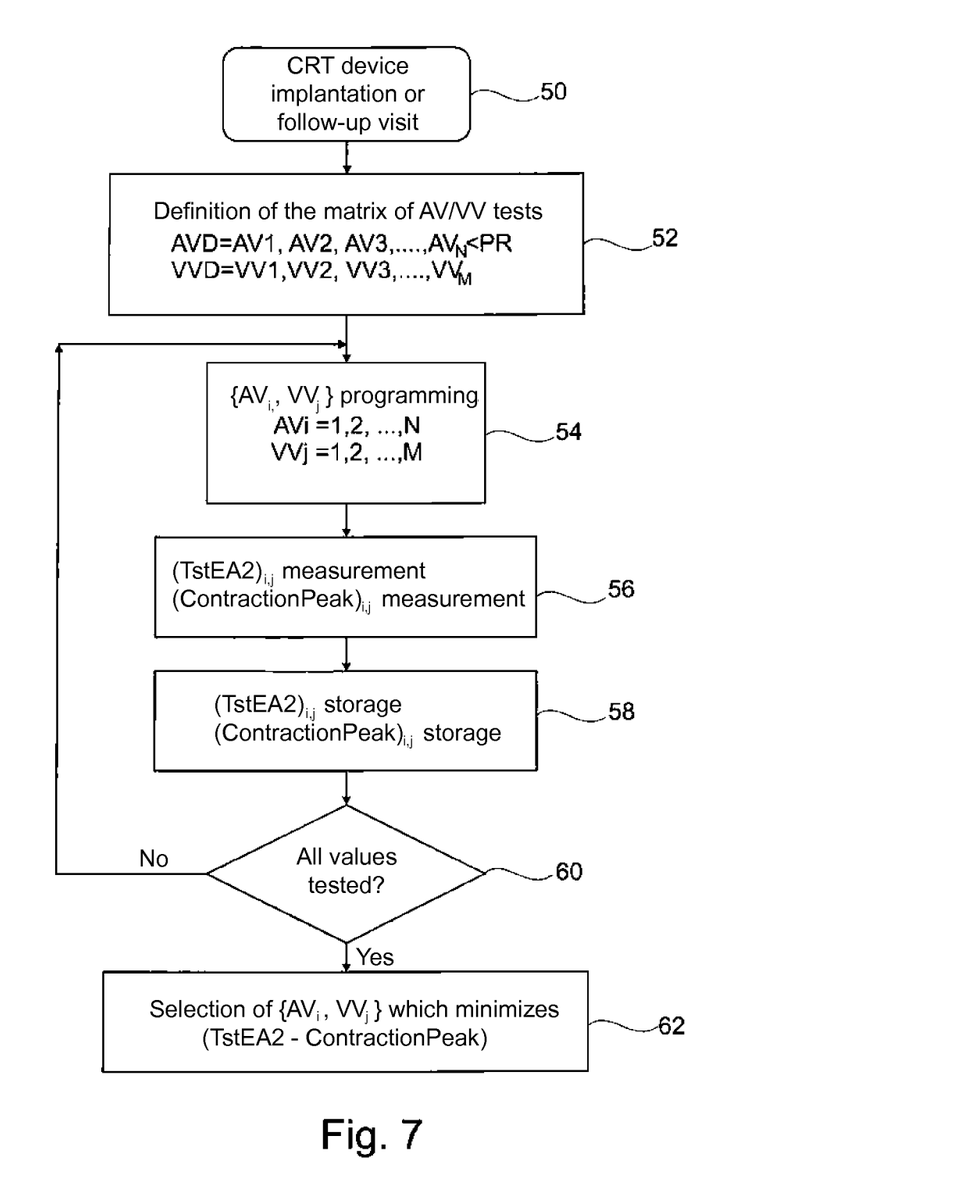
FIG. 7 is a flow chart of a process for diagnosis and treatment of temporal ventricular desynchronization according to an exemplary embodiment.

Referring now to FIG. 7, a flowchart illustrating the various steps of a method for the diagnosis and treatment of temporal ventricular desynchronization is shown, according to an exemplary embodiment. At the implantation of the device or at a later follow-up visit to the physician (step 50), the device sets a test matrix with different combinations of possible atrioventricular (AVD) and interventricular (VVD) delays (step 52).

In steps 54-60, the device tests various combinations of AVD and VVD values. The device is programmed with each of these pairs of delays $\{AV_i, VV_j\}$ (step 54). The device applies a pair of values and measures the corresponding time $T_{stEA2ij}$ (representative of the closing time of the aortic valve AC) and the time of the contraction peak (representative of the moment when all segments of the left ventricle wall have finished contracting) (step 56). The collected values are stored (step 58) and the device passes to the following pair of set values (step 60). Steps 54-60 may be repeated until all pairs of values $\{AV_i, VV_j\}$ in the test matrix have been programmed and tested.

Once all the pairs of values in the test matrix have been tested, the device selects the pair among these pairs of values that minimizes the temporal difference between the reference marker $T_{stEA2ij}$ and the contraction peak of the left ventricle (step 62). Ideally, the device selects the pair of values that completely eliminates the temporal difference between the reference marker $T_{stEA2ij}$ and the contraction peak of the left ventricle.

The combination of AVD and VVD that provide the minimal temporal difference between the reference marker $T_{stEA2ij}$ and the contraction peak of the left ventricle may represent the best condition of temporal resynchronization. A minimum difference that is slightly positive or zero indicates that it can be expected that all segments, or virtually all segments, of the wall of the left ventricle are contracted before the closure of the aortic valve. A negative minimum difference means that, although the temporal resynchronization has been improved, the ventricular segments do not all contract before the closure of the aortic valve.

In the case of a fully implanted device, this adjustment test of AVD and VVD can be automatically repeated (e.g., weekly, monthly, etc.) to take into account possible changes of the patient's situation. Repeating the process illustrated in FIG. 7 may be useful to account for ventricular remodeling or for any other reason that would again provoke diastolic contraction.

The diagnostic method described herein can be used in combination with algorithms for automatic optimization of AVD and VVD such as those described in European Patent Application No. 2357020 A1 (Sorin CRM), which analyzes the typical sigmoid characteristic of variation of the AVD, and/or in the European Patent Application No. 1736203 A1 (Sorin CRM) which evaluates an hemodynamic performance index as a function of the area enclosed by this characteristic. If the difference between the timing values generated by the optimization algorithm (i.e., the algorithm disclosed in the above-referenced patents) and the timing values generated by the present invention (i.e., the pair {AVD, VVD} that minimizes the temporal difference between the reference marker and the contraction peak of the left ventricle) is negative or zero, there is no proven temporal desynchronization and the values of AVD and VVD calculated by the algorithm can be selected as optimal. However, if this difference is positive, the test of other values of AVD and VVD than those proposed by the optimization algorithm can improve the temporal resynchronization, with minimal impact on the spatial resynchronization.

The invention claimed is:

1. A method for evaluating and treating a temporal ventricular desynchronization in a heart of a patient, the method comprising:
   receiving a signal representative of a blood flow in a left chamber of the heart;
   receiving a signal representative of a displacement of a left ventricle of the heart;
   determining an instant of closure of an aortic valve using the signal representative of the blood flow in the left chamber;
   determining a peak of contraction of the left ventricle using the signal representative of the displacement of the left ventricle;
   calculating a temporal shift between an instant of the peak of contraction of the left ventricle and the instant of closure of the aortic valve;
   selecting a current stimulation configuration based on the calculated temporal shift; and
   delivering stimulation pulses to be applied to electrodes respectively implanted in at least one right ventricular pacing site and at least one left ventricular pacing site according to the current stimulation configuration based on the calculated temporal shift.

2. The method of claim 1, wherein the current stimulation configuration comprises delay values for at least one of an inter-ventricular delay and an atrioventricular delay;
   the method further comprising adjusting at least one of the inter-ventricular delay and the atrioventricular delay to minimize the temporal shift.

3. The method of claim 2, wherein adjusting at least one of the inter-ventricular delay and the atrioventricular delay comprises:
   increasing at least one of the inter-ventricular delay and the atrioventricular delay if the instant of the peak of contraction of the left ventricle is later than the instant of the closure of the aortic valve.

4. The method of claim 2, wherein receiving a signal representative of a blood flow in a left chamber of the heart comprises:
   receiving an endocardial acceleration signal from a hemodynamic sensor configured to measure a blood flow in a left chamber of the heart;
   wherein the hemodynamic sensor includes at least one of: an implantable or external endocardial acceleration sensor, an implantable bioimpedance sensor, an implantable or external T wave detection sensor, and an implantable ventricular pressure sensor.

5. The method of claim 2, wherein receiving a signal representative of a blood flow in a left chamber of the heart comprises receiving an endocardial acceleration signal from an implantable hemodynamic sensor configured to measure a blood flow in a left chamber of the heart;
   wherein determining an instant of closure of an aortic valve comprises:
      identifying a portion of the endocardial acceleration signal corresponding to a period of endocardial acceleration associated with an isovolumetric ventricular relaxation; and
      using an instant corresponding to a beginning of the identified portion of the endocardial acceleration signal as the instant of closure of the aortic valve.

6. A method for evaluating and treating a temporal ventricular desynchronization in a heart of a patient, the method comprising:
- receiving a signal representative of a blood flow in a left chamber of the heart;
- receiving a signal representative of a displacement of a left ventricle of the heart;
- determining an instant of closure of an aortic valve using the signal representative of the blood flow in the left chamber;
- determining a peak of contraction of the left ventricle using the signal representative of the displacement of the left ventricle;
- calculating a temporal shift between an instant of the peak of contraction of the left ventricle and the instant of closure of the aortic valve; and
- delivering stimulation pulses to be applied to electrodes respectively implanted in at least one right ventricular pacing site and at least one left ventricular pacing site according to a current stimulation configuration, wherein the current stimulation configuration is based on the calculated temporal shift;
- wherein the current stimulation configuration comprises delay values for at least one of an inter-ventricular delay and an atrioventricular delay;
- the method further comprising adjusting at least one of the inter-ventricular delay and the atrioventricular delay to minimize the temporal shift;
- wherein receiving a signal representative of a blood flow in a left chamber of the heart comprises receiving an endocardial acceleration signal from an implantable hemodynamic sensor configured to measure a blood flow in a left chamber of the heart;
- wherein determining the instant of closure of the aortic valve comprises:
  - calculating an energy envelope, wherein the energy envelope is a function of the endocardial acceleration signal;
  - identifying a time at which a magnitude of the energy envelope crosses a threshold energy value; and
  - using the time at which the magnitude of the energy envelope crosses the threshold energy value as the instant of closure of the aortic valve.

7. A method for evaluating and treating a temporal ventricular desynchronization in a heart of a patient, the method comprising:
- determining an instant of closure of an aortic valve and a peak of contraction of a left ventricle of the heart using measurement signals received from an implantable myocardial stimulation device;
- calculating a temporal shift between the instant of closure of the aortic valve and an instant of the peak of contraction of the left ventricle;
- selecting a stimulation configuration based on the calculated temporal shift, the stimulation configuration comprising delay values for at least one of an inter-ventricular delay and an atrioventricular delay; and
- operating the implantable stimulation device to deliver stimulation pulses to electrodes implanted in at least one right ventricular pacing site and at least one left ventricular pacing site according to the selected stimulation configuration.

8. The method of claim 7, wherein determining the instant of closure of the aortic valve comprises:
- receiving an endocardial acceleration signal from an implantable hemodynamic sensor configured to measure a blood flow in a left chamber of the heart;
- identifying a portion of the endocardial acceleration signal corresponding to a period of endocardial acceleration associated with an isovolumetric ventricular relaxation; and
- using an instant corresponding to a beginning of the identified portion of the endocardial acceleration signal as the instant of closure of the aortic valve.

9. The method of claim 7, wherein determining the instant of closure of the aortic valve comprises:
- receiving an endocardial acceleration signal from an implantable hemodynamic sensor configured to measure a blood flow in a left chamber of the heart;
- calculating an energy envelope, wherein the energy envelope is a function of the endocardial acceleration signal;
- identifying a time at which a magnitude of the energy envelope crosses a threshold energy value; and
- using the time at which the magnitude of the energy envelope crosses the threshold energy value as the instant of closure of the aortic valve.

10. The method of claim 9, further comprising calculating the threshold energy value, wherein calculating the threshold energy value comprises:
- determining a maximum energy associated with the energy envelope;
- identifying an energy value corresponding to a predetermined fraction of the maximum energy; and
- using the identified energy value as the threshold energy value.

11. The method of claim 7, wherein determining the instant of the peak of contraction of the left ventricle comprises:
- receiving a measurement signal from at least one motion sensor configured to measure a displacement of the left ventricle wall;
- identifying an instant at which the measurement signal from the at least one motion sensor is at an extremum; and
- using the instant at which the measurement signal from the at least one motion sensor is at an extremum as the instant of the peak of contraction of the left ventricle.

12. The method of claim 7, further comprising:
- receiving measurement signals from at least two motion sensors configured to measure a displacement of a left ventricle wall and a right ventricle wall;
- determining an instant corresponding to a peak of contraction of the left ventricle and an instant corresponding to a peak of contraction of a right ventricle based on the measurement signals from the at least two motion sensors; and
- identifying a spatial desynchronization based on a temporal shift between the instants of the peaks of contraction of the left and right ventricles.

* * * * *